United States Patent
Olsson et al.

(10) Patent No.: US 9,393,185 B2
(45) Date of Patent: *Jul. 19, 2016

(54) CLEANSING COMPOSITION

(75) Inventors: Kristin Olsson, Ladenburg (DE);
Martin Hoffmann, Zwingenberg (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/124,399

(22) PCT Filed: May 22, 2012

(86) PCT No.: PCT/EP2012/059431
§ 371 (c)(1),
(2), (4) Date: Jan. 29, 2014

(87) PCT Pub. No.: WO2012/168061
PCT Pub. Date: Dec. 13, 2012

(65) Prior Publication Data
US 2014/0215727 A1    Aug. 7, 2014

(30) Foreign Application Priority Data

Jun. 10, 2011 (EP) .................................. 11169432

(51) Int. Cl.
*A61K 8/42* (2006.01)
*A61K 8/46* (2006.01)
*A61Q 5/00* (2006.01)
*A61Q 5/02* (2006.01)
*A61Q 5/12* (2006.01)
*A61K 8/37* (2006.01)
*A61Q 5/10* (2006.01)

(52) U.S. Cl.
CPC ... *A61K 8/42* (2013.01); *A61K 8/37* (2013.01); *A61K 8/466* (2013.01); *A61Q 5/004* (2013.01); *A61Q 5/02* (2013.01); *A61Q 5/10* (2013.01); *A61Q 5/12* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 4,676,978 A * | 6/1987 | Cseh | 510/121 |
| 5,227,086 A | 7/1993 | Kacher et al. | |
| 6,013,616 A | 1/2000 | Fabry et al. | |
| 6,284,230 B1 * | 9/2001 | Sako et al. | 424/70.11 |
| 2002/0187915 A1 | 12/2002 | Sakai et al. | |
| 2003/0172474 A1 | 9/2003 | Lang et al. | |
| 2004/0224863 A1 | 11/2004 | Sun et al. | |
| 2005/0031570 A1 * | 2/2005 | Grit et al. | 424/70.31 |
| 2007/0081953 A1 | 4/2007 | Dahms | |
| 2008/0189876 A1 * | 8/2008 | Trigg et al. | 8/405 |

FOREIGN PATENT DOCUMENTS

| | | |
|---|---|---|
| DE | 44 32 366 A1 | 3/1996 |
| DE | 102 13 574 A1 | 10/2002 |
| EP | 0 559 375 A1 | 9/1993 |
| EP | 1 925 290 A1 | 5/2008 |
| WO | 2012/168060 A1 | 12/2012 |

OTHER PUBLICATIONS

International Search Report dated Jun. 6, 2012, mailed Jun. 26, 2012.

* cited by examiner

*Primary Examiner* — Necholus Ogden, Jr.
(74) *Attorney, Agent, or Firm* — Norris McLaughlin & Marcus PA

(57) ABSTRACT

Present invention relates to an aqueous cleansing composition for keratin fibres, especially human hair, comprising at least one mono ester anionic surfactant, at least one anionic amide surfactant, at least one anionic surfactant which is different from the foregoing two surfactants and the composition is substantially free from amphoteric surfactant.

13 Claims, No Drawings

CLEANSING COMPOSITION

This application is a 371 application of PCT/EP2012/059431 filed May 22, 2012, which claims foreign priority benefit under 35 U.S.C. §119 of European Application No. 11169432.9 filed Jun. 10, 2011.

Present invention relates to an aqueous cleansing composition for keratin fibres, especially human hair, comprising at least one mono ester anionic surfactant, at least one anionic amide surfactant, at least one anionic surfactant which is different from the foregoing two surfactants and the composition is substantially free of amphoteric surfactant.

Cleansing compositions have been known for many years. Many patent applications and scientific publications deal with such compositions aiming at cleansing, especially improved conditioning effects after cleansing. Cleansing compositions wash out dirt on the hair and at the same time dyestuffs deposited onto or into hair are also washed out, which leads to shorter colour durability after coloration services and is not economical in terms of frequent hair dressing need and also health of hair. Attempts have been made to reduce colour wash out from coloured hair with various ways. One of them is so called colour sealing which requires application of an additional mostly hydrophobic composition right after colouring hair so that the dyes are not easily solubilised by the high surfactant content of cleansing compositions. The other approach has been to use a special surfactant combination which interacts with dyestuff molecules and also with hair in a lesser extent. None of the approaches are optimal for variably coloured hair and, therefore, there is a great need for further improvements in the field.

Aim of the present invention is to provide an aqueous cleansing composition having optimal benefits of foam properties in terms of its volume and creaminess as well as improved conditioning effects on keratin fibres, especially human hair, in terms of combability, smoothness, elasticity, softness, volume and body and at the same time washes out artificial hair colour in a lesser extend so that the coloured hair keeps its colour and therefore shine and healthy appearance.

Present inventors have surprisingly found that an aqueous cleansing composition comprising at least one mono ester anionic surfactant, at least one anionic amide surfactant, at least one anionic surfactant which is different from the foregoing two surfactants and the composition is substantially free of amphoteric surfactant, provides excellent foam and conditioning properties and also washes out less colour from hair so that long lasting colours are achieved.

Accordingly, the first object of the present invention is an aqueous cleansing composition comprising at least one mono ester anionic surfactant, at least one anionic amide surfactant, at least one anionic surfactant which is different from the foregoing two surfactants and the composition is substantially free of amphoteric surfactant.

With the term mono ester anionic surfactant it is meant that the anionic surfactant includes only one ester group in its molecule.

With the term anionic amide surfactant it is meant that the anionic surfactant comprise at least one amide group in its molecule and especially those surfactants are meant derived from taurate, glutamate, alanin or alaninate, sarcosinate and aspartate.

With the term amphoteric surfactant any surfactant is meant which is amphoteric in the composition it is comprised.

Second object of the present invention is the use of cleansing composition comprising at least one mono ester anionic surfactant, at least one anionic amide surfactant, at least one anionic surfactant which is different from the foregoing two surfactants and the composition is substantially free of amphoteric surfactant for cleansing and conditioning hair.

Third objective of the present invention is the use of cleansing composition comprising at least one mono ester anionic surfactant, at least one anionic amide surfactant, at least one anionic surfactant which is different from the foregoing two surfactants and the composition is substantially free of amphoteric surfactant, for reducing colour fading and/or wash out from artificially coloured hair.

Further object of the present invention is a kit for treating hair wherein it comprises two or more compositions wherein at least one of the compositions is a composition according to present invention.

Still further object of the present invention is a process for treating hair wherein hair is artificially coloured in a first step and washed with a cleansing composition of the present invention.

Compositions of the present invention comprises surfactant at a total concentration of 5 to 50%, preferably 7.5 to 40%, more preferably 8 to 30% and most preferably 10 to 25% and particularly 10 to 20% by weight, calculated to the total of the composition.

Cleansing composition of the present invention comprises at least one mono ester anionic surfactant, which is preferably according to the general structure

$$R_{30}C(O)OR_{31}SO_3M$$

wherein $R_{30}$ is a saturated or unsaturated, straight or branched alkyl chain with 9 to 17 C atoms, $R_{31}$ is a methyl or straight or branched alkyl chain with 2 to 4 C atoms and M is ammonium or an alkali metal, preferably sodium.

Suitable non-limiting examples are sodium cocoyl isethionate, sodium lauroyl isethionate, sodium oleoyl isethionate, sodium oleoyl methyl isethionate, sodium lauroyl methyl isethionate, sodium stearoyl isethionate, sodium stearoyl methyl isethionate and ammonium cocoyl isethionate. Preferred are sodium cocoyl isethionate and ammonium cocoyl isethionate.

Concentration of at least one mono ester anionic surfactant is in the range of 1 to 15%, preferably 2 to 12%, more preferably 3 to 10% and most preferably 3 to 7.5% by weight calculated to the total content of the composition. The concentrations mentioned here are total concentration ranges in case more than one mono ester anionic surfactant is present.

Composition of the present invention comprises at least one anionic amino acid surfactant of the following structure

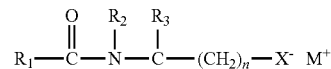

wherein $R_1$ is a saturated or unsaturated, straight or branched alkyl chain with 7 to 17 C atoms, $R_2$ is H or a methyl, $R_3$ is H, $COO^-M^+$, $CH_2COO^-M$ or $COOH$, n is 0 to 2, X is $COO^-$ or $SO_3^-$ and M is independent from each other H, sodium, potassium or ammonium. In the preferred embodiment of the present invention $R_1$ is a saturated or unsaturated, straight or branched alkyl chain with 9 to 17 C atoms, and more preferably 9 to 13 C atoms, $R_2$ is H or a methyl, $R_3$ is H, $COO^-M^+$, $CH_2COO^-M$ or $COOH$, n is 0 to 2, X is $COO^-$ or $SO_3^-$ and M is independent from each other H, sodium, potassium or ammonium. It should be noted that alkyl chain includes also mixture of various alkyl groups as present especially in plant triglyceride derived alkyl chains such as cocoyl chain.

Cleansing composition of the present invention comprises at least one anionic amino acid surfactant according to the general formula of above at a concentration of 1 to 15%, preferably 2 to 12%, more preferably 3 to 10% and most preferably 3 to 7.5% by weight calculated to the total content of the composition. The concentrations mentioned here are total concentration ranges in case more than one amino acid surfactant is present.

Suitably amino acid surfactant types are taurate, glutamate, alanin or alaninate, sarcosinate, aspartate surfactants, and mixtures thereof. Preferred are taurate, glutamate and sarcosinate surfactants and mixtures thereof. More preferred are taurates and glutamates and most preferred is glutamate type surfactants.

Suitable taurate surfactants are according to the general formula

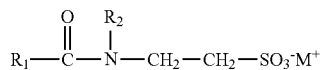

wherein $R_1$ is preferably a saturated or unsaturated, straight or branched alkyl chain with 7 to 17 C atoms, and more preferably 9 to 13 C atoms, $R_2$ is H or methyl, and M is H, sodium or potassium. Suitable examples are potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, and sodium methyl stearoyl taurate and mixtures thereof. Preferred are potassium cocoyl taurate, potassium methyl cocoyl taurate, sodium caproyl methyl taurate, sodium cocoyl taurate, sodium lauroyl taurate, sodium methyl cocoyl taurate and sodium methyl lauroyl taurate and mixtures thereof. More preferred are potassium cocoyl taurate, potassium methyl cocoyl taurate, sodium cocoyl taurate, sodium lauroyl taurate, sodium methyl cocoyl taurate and sodium methyl lauroyl taurate and mixtures thereof.

Suitable glutamate surfactants are according to the general formula

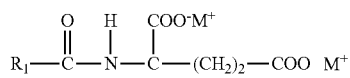

wherein $R_1$ is preferably a saturated or unsaturated, straight or branched alkyl chain with 7 to 17 C atoms, and more preferably 9 to 13 C atoms, and M is independent from each other H, sodium or potassium. Suitable examples are dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof. Preferred are disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, and sodium myristoyl glutamate and mixtures thereof. More preferred are disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, and sodium lauroyl glutamate and mixtures thereof.

Suitable alanine or alaninate surfactants are according to the general formula

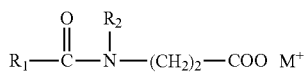

wherein $R_1$ is preferably a saturated or unsaturated, straight or branched alkyl chain with 7 to 17 C atoms, and more preferably 9 to 13 C atoms, $R_2$ is H or methyl and M is H, sodium or potassium. Suitable examples are cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine and mixtures thereof.

Suitable glycine surfactants are according to the general formula

wherein $R_1$ is preferably a saturated or unsaturated, straight or branched alkyl chain with 7 to 17 C atoms, and more preferably 9 to 13 C atoms, and M is H, sodium or potassium. Suitable examples are palmitoyl glycine, sodium lauroyl glycine, sodium cocoyl glycine, sodium myristoyl glycine, potassium lauroyl glycine, and potassium cocoyl glycine and mixtures thereof.

Suitable sarcosinate surfactants are according to the general formula

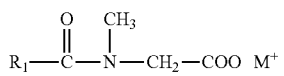

wherein $R_1$ is preferably a saturated or unsaturated, straight or branched alkyl chain with 7 to 17 C atoms, and more preferably 9 to 13 C atoms, and M is H, sodium or potassium. Suitable examples are potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof. Preferred are potassium lauroyl sarcosinate, potassium cocoyl sarcosinate, sodium cocoyl sarcosinate, and sodium lauroyl sarcosinate and mixtures thereof. More preferred are sodium cocoyl sarcosinate, and sodium lauroyl sarcosinate and mixtures thereof.

Suitable aspartate surfactants are according to the general formula

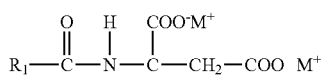

wherein $R_1$ is preferably a saturated or unsaturated, straight or branched alkyl chain with 7 to 17 C atoms, and more preferably 9 to 13 C atoms, and M is independent from each other H, sodium or potassium. Suitable examples are sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, and dipotassium caproyl aspartate and mixtures thereof. Preferred are sodium lauroyl aspartate, sodium myristoyl aspartate, sodium cocoyl aspartate, and sodium caproyl aspartate and mixtures thereof.

It should be noted that compositions of the present invention can also comprise mixture of several type of amino acid surfactants such as mixture of glutamate and taurate surfactants, or mixture of taurate, glutamate and sarcosinate surfactants etc.

Composition of the present invention comprises at least one additional anionic surfactant which is different from the two foregoing anionic surfactants. In principal any anionic surfactant other than mentioned above is suitable within the meaning of the present invention. Especially suited and preferred anionic surfactants are alkyl ether sulphates according to the general structure

$R_{40}(OCH_2CH_2)_nOSO_3M$ wherein $R_{40}$ is a straight or branched, saturated or unsaturated alkyl chain with 8 to 22 C atoms, preferably with 10 to 18 C atom and more preferably 12 to 14 C atoms, n is a number between 1 to 4 and M is an alkali metal such as sodium or potassium and ammonium.

Non-limiting examples are sodium laureth sulphate, ammonium laureth sulphate, sodium oleth sulphate, sodium myreth sulphate and sodium deceth sulphate. Especially preferred is sodium laureth sulphate.

Further suitable anionic surfactants are of the sulfonate, carboxylate and alkyl phosphate types, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $R_7$—$(C_2H_4O)_n$—$O$—$CH_2COOX$, wherein $R_7$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

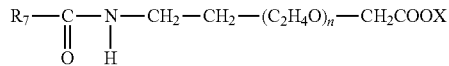

wherein R and X have the above meanings, and n is in particular a number from 1 to 10, preferably 2.5 to 5.

Such products have been known for some time and are on the market, for example, under the trade name "AKYPO®" and "AKYPO-SOFT®".

Concentration of at least one additional anionic surfactant other than the foregoing two types of anionic surfactant is in the range of 1 to 15%, preferably 2 to 12%, more preferably 3 to 10% and most preferably 3 to 7.5% by weight calculated to the total content of the composition. The concentrations mentioned here are total concentration ranges in case more than one anionic surfactant other than the foregoing two types is present.

Composition of the present invention comprises preferably at least one non-ionic surfactant. Nonionic surfactants are comprised at a concentration of 1% to 15%, preferably from 1% to 10% by weight, calculated to the total composition.

Nonionic surfactants preferred in the cleansing compositions according to the invention are alkyl polyglucosides of the general formula

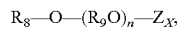

$R_8$—$O$—$(R_9O)_n$—$Z_X$, wherein $R_8$ is an alkyl group with 8 to 18 carbon atoms, $R_9$ is an ethylene or propylene group, Z is a saccharide group with 5 to 6 carbon atoms, n is a number from 0 to 10 and x is a number between 1 and 5. Especially suited examples are decyl polyglucoside, cocoyl polyglucoside and lauryl polyglucoside.

Further nonionic surfactants are long-chain fatty acid dialkanolamides, such as coco fatty acid diethanolamide and myristic fatty acid diethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylate. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

The more preferred non-ionic surfactants are alkyl polyglucosides such as decyl, cocoyl polyglucoside and ethoxylated fatty alcohols such as laureth-16. Especially preferred are alkyl polyglucosides such as decyl, cocoyl polyglucoside.

In a further preferred embodiment, cleansing composition of the present invention comprises hair-conditioning agents. Conditioning agents can be selected from oily substances, non-ionic substances, cationic amphiphilic ingredients, cationic polymers other than the one described above or their mixtures.

Oily substances are selected from such as silicone oils, either volatile or non-volatile, natural and synthetic oils.

Among silicone oils those can be added to the compositions include dimethicone, dimethiconol, polydimethylsiloxane, DC fluid ranges from Dow Corning, arylated silicones such as phenyl trimethicone or any other silicone with up to 5 aryl, preferably phenyl, group in its molecule such as trimethyl pentaphenyl trisiloxane, natural oils such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents can be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $$R_{11}CO(OCH_2CH_2)_nOH$$

or $$R_{11}CO(OCH_2CH_2)_nOCR_{12}$$

where $R_{11}$ and $R_{12}$ are independent from each other saturated, unsaturated or branched or non-branched alkyl chain with 7 to 21 C atoms and n is typically 2-100.

In one of the preferred form of the present invention, cleansing compositions comprise at least one additional cationic polymer as a conditioning agent. Suitable cationic polymers are those of best known with their CTFA category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, and Polyquaternium 86.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic tara gum an its derivatives known with INCI name Caesalpinia spinosa hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic Caesalpinia spinosa gum derivatives, polyquaternium 6, polyquaternium 7, polyquaternium 67 and polyquaternium 70. The cationic polymers also include the quaternized products of graft polymers from organopolysiloxanes and polyethyl oxazolines described in EP-A 524 612 and EP-A 640 643.

Composition of the present invention comprises cationic polymer at a concentration of 0.01 to 5%, preferably 0.02 to 4%, more preferably 0.05 to 3% and most preferably 0.1 to 2.5% by weight calculated to total composition.

Although less preferred, cleansing compositions of the present invention may comprise additionally one or more cationic surfactant(s) as conditioner according to the general formula $$R_{13}-\underset{\underset{R_{16}}{|}}{\overset{\overset{R_{14}}{|}}{N^+}}-R_{15}\ X^-$$

where $R_{13}$ is a saturated or unsaturated, branched or non-branched alkyl chain with 8-24 C atoms or $$R_{17}CONH(CH_2)_n$$

where $R_{17}$ is saturated or unsaturated, branched or non-branched alkyl chain with 7-21 C atoms and n has value of 1-4, or $$R_{18}COO(CH_2)_n$$

where $R_{18}$ is saturated or unsaturated, branched or non-branched alkyl chain with 7-21 C atoms and n has value of 1-4, and $R_{14}$ is unsaturated or saturated, branched or non-branched alkyl chain with 1-24 C atoms or $$R_{17}CONH(CH_2)_n$$

or $$R_{18}COO(CH_2)_n$$

where $R_{17}$, $R_{18}$ and n are same as above.

$R_{15}$ and $R_{16}$ are lower alkyl chain with 1 to 4 carbon atoms which may be substituted with one or more hydroxyl groups, and X is anion such as chloride, bromide, methosulfate.

Typical examples of those ingredients are cetyl trimethly ammonium chloride, stear trimonium chloride, behentrimonium chloride, stearamidopropyl trimonuim chloride, dioleoylethyl dimethyl ammonium methosulfate, dioleoylethyl hydroxyethylmonium methosulfate.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Typical concentration range for any of those conditioners of cationic polymers, silicone oil and derivatives and cationic surfactants is in the range of 0.01 to 5% by weight, preferably 0.01 to 3.5% by weight, more preferably 0.05 to 2.5% and most preferably 0.1 to 1.5% by weight calculated to the total composition. Most preferred conditioning agents are cationic polymers.

In another preferred form of the invention, aqueous cleansing composition comprises at least one organic solvent such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, polypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzyl alcohol and polypropylene glycols. Total concentration of organic solvents in the shampoo composition should not exceed 5% by weight, preferably in the range of 0.1 to 3%, more preferably 0.5 to 2.5% by weight calculated to total composition.

Aqueous cleansing composition of the present invention may further comprise at least one fatty alcohol of the following formula

wherein $R_6$ is straight or branched, saturated or unsaturated alkyl chain with 8 to 24, preferably 10 to 22, more preferably 12 to 18 and most preferably 12 to 16 C atoms at a concentration of 0.1 to 5%, preferably 0.1 to 4% and more preferably 0.25 to 3% and most preferably 0.5 to 2.5% by weight calculated to total composition.

Suitable non-limiting preferred examples are decyl alcohol, myristyl alcohol, lauryl alcohol, cetyl alcohol, stearyl alcohol, behenyl alcohol, and arachidyl alcohol and their mixtures. More preferred are decyl alcohol, myristyl alcohol, lauryl alcohol, cetyl alcohol, and stearyl alcohol. Most preferred are decyl alcohol, myristyl alcohol and lauryl alcohol, and their mixtures.

Cleansing composition of the present invention may have pearly appearance. Pearl-shiny appearance is achieved with those dispersed in cleansing conditioning compositions in crystalline form, i.e. so called pearl-shine or pearlizing agents. The preferred once are PEG-3 distearate and ethylene glycol distearate. The concentration of those can typically be from 0.1 to 3%, preferably 0.5 to 2% by weight, calculated to the total composition. These compounds are preferably added to the compositions in admixture with anionic, nonionic and/or amphoteric surfactants. Such kinds of mixtures are available commercially.

Solubilizers may be added to the compositions especially when oily substances are chosen as conditioning agents and fragrance oils with highly lipophilic properties. Typical solubilizers may be hydrogenated castor oil known with the trade mark Cremophor CO series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

The cleansing composition may contain active ingredients selected from UV filters, moisturisers, sequestering agents, and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are preferably selected from polycarboxy acids. The preferred one is ethylene diamine tetraacetic acid, EDTA. Typical useful concentration range for sequestering agents is of 0.01-2.5% by weight calculated to the total composition.

The UV filters are that oil and water soluble ones for the purpose of protecting hair and hair colour. In other words, anionic and non-ionic, oily UV filters are suitably used in the compositions of the present invention. Suitable UV-absorbing substances is are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxybenzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof, 3-(4'-methyl benzylidene)-DL-campher, and/or polysilicone-15. The amount of the UV-absorber ranges typically from about 0.01% to 2.5%, more preferably from 0.05% to 1% by weight, calculated to the total composition.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, various "Extrapone®" products, and "Herbasol®". Extracts and the preparation thereof are also described in "Hagers Handbuch der pharmazeutischen Praxis", $4^{th}$ Ed.

Compositions of the present invention may comprise further at least one compound according to the formula

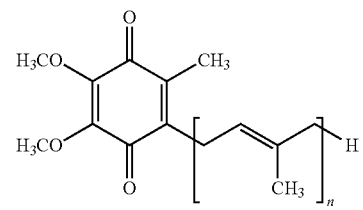

where n is a number from 1 to 10.

The compounds of the above formula are known as Ubiquinone, and also are known as Coenzyme. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

Cleansing compositions of the present invention can also comprise synthetic mica as a further shine enhancer. Suitable metal oxide or oxides for coating synthetic mica are titanium dioxide, chromium oxide, ferric oxide or mixtures thereof. In the present invention the preferred is synthetic mice coated with titanium dioxide. Such materials are commercially available from Sun Chemical Corporation and known with their INCI names Synthetic Fluorphologopite. Concentration of synthetic mica coated with at least metal oxide or oxides is from 0.001 to 10%, preferably 0.05 to 7.5%, more preferably 0.1 to 5% and most preferably 0.20 to 2.5% by weight calculated to total composition.

Further in a preferred embodiment of the present invention, compositions comprise at least one direct dye and as well deposit dyestuffs onto hair. Suitable direct dyes are of cationic, anionic and neutral nitro dyes. It should be noted that they can also be used in combination with each other. In other words a composition according to present invention can comprise an anionic and a cationic dye as well as an anionic and a nitro dye or a cationic and a nitro dye. Certainly the combination of all three dyestuff categories is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and mixtures thereof.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and mixtures thereof.

Among those, the preferred anionic dyestuffs are Acid Red 52, Acid Violet 2, Acid Red 33, Acid Orange 4, Acid Red 27 and Acid Yellow 10 and their salts, and mixtures thereof. The most preferred anionic dyes are Acid Red 52, Acid Violet 2, Acid Red 33, Acid Orange 4 and Acid Yellow 10, and their salts, and mixtures thereof.

Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and mixtures thereof.

Concentration of one or more direct dyes in total is in the range of 0.001 to 5% by weight, preferably 0.01 to 4% more preferably 0.05 to 3% and most preferably 0.1 to 2.5% by weight calculated to total composition. The most preferred among the direct dyes is cationic direct dyes.

It is self-understood that the shampoos according to the invention may comprise other substances customarily used in such compositions such as preservatives, fragrances.

The pH of the compositions according to the present invention is suitably between 2 and 8.0, preferably in the range of 2.5 to 7.0, more preferably 3 to 6.5 and most preferably 4 to 5.5 measured at ambient temperature with a suitable pH meter.

pH of the compositions is adjusted with acidic and alkaline compounds. Acidic compounds can be inorganic and organic acid or their mixtures. Nonlimiting suitable examples are citric acid, lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. Alkaline compounds such as sodium hydroxide can be used to adjust the pH of the compositions.

Aqueous cleansing composition of the present invention preferably comprises one or more thickeners. Suitable ones are ethoxylated polyglyceryl esters with total ethoxy units in the range of 50 to 200 and fatty acyl chain length of 8 to 22 C atoms such as PEG-80 glyceryl cocoate, PEG-90 glyceryl isostearate, PEG-120 glyceryl stearate, PEG-200 glyceryl stearate, PEG-80 glyceryl tallowate, PEG-82 glyceryl tallowate, PEG-130 glyceryl tallowate, and PEG-200 glyceryl tallowate, gylceryl oleate/cocoate and inorganic salt in particular sodium chloride when especially composition comprise alkyl ether sulphate type of surfactants.

It has especially been found out that aqueous cleansing compositions of the present invention are successfully thickened with compounds according to general structure

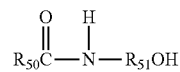

wherein $R_{50}$ is a straight or branched, saturated or unsaturated alkyl chain with 11 to 21 C atoms and is a straight or branched alkyl chain with 1 to 4 C atoms. Suitable and most preferred example is isostearamide MIPA.

Cleansing compositions of the present invention preferably has a viscosity in the range of 500 to 20,000 mPa·s, more preferably 1,000 to 15,000 mPa·s and most preferably 1,500 to 10,000 mPa·s measured at 20° C. with a Brookfield viscosimetre using from example Spindle 5 at appropriate rotation speed.

The following examples are to illustrate the invention, but not to limit. The products according to the invention are prepared by mixing the individual components in water, whereby it is also possible to use pre-mixtures of various ingredients.

EXAMPLE 1

TABLE I

Comparative aqueous cleansing compositions

| | % by weight | | | | |
|---|---|---|---|---|---|
| | A | B | C | D | E |
| Sodium cocoyl isethionate | 6 | — | 9 | 5 | 5 |
| Sodium laureth sulphate | 6 | 9 | — | 5 | 5 |
| Coco glucoside | — | — | — | 3 | 3 |
| Sodium lauroyl glutamate | 6 | 9 | 9 | 5 | 5 |
| Polyqauternium-10 | — | — | — | — | 0.5 |
| Citric acid | q.s to pH 5.0 | | | | |
| Preservative, fragrance | q.s. | | | | |
| Water | q.s. to 100 | | | | |

Shampoo compositions A, D to E are according to the invention and B and C represent a comparative composition.

Hair tresses were coloured with a commercially available oxidative colouring composition comprising oxidative and direct dyes. The tresses so coloured were washed 10 times with above compositions and before starting the test and afterwards L, a and b values were measured. With the help of the known equation ΔE values were calculated to present colour difference numerically.

Results are presented in Table II.

TABLE II

Results of colour wash out test.

| Composition | ΔE |
|---|---|
| A | 4.3 |
| B | 7.4 |
| C | 6.8 |
| D | 4.1 |
| E | 3.5 |

It should be noted that the higher the ΔE value the larger the colour difference between the two tresses. In the opposite, the smaller the ΔE value the smaller the colour difference between the two tresses. From the above results, it is clear that cleansing composition comprising the three surfactants produces lower ΔE values. The following compositions delivered similar colour wash out data.

EXAMPLE 2

| | % by weight |
|---|---|
| Sodium lauryl ether sulphate | 5.5 |
| Sodium lauroyl glutamate | 4.5 |
| Decyl glucoside | 3.0 |
| Sodium cocoyl isethionate | 5.0 |
| Polyquaternium-7 | 0.5 |
| Isostearamide MIPA | 2.0 |
| Citric acid/sodium hydroxide | q.s. to pH 5.5 |
| Preservative, fragrance | q.s |
| Water | to 100 |

The above shampoo was judged to have rich and creamy foam in a monadic test by the volunteers. It was furthermore mentioned that it foams very quickly. Additionally, the hair washed was excellently combable and had good shine.

EXAMPLE 3

| | % by weight |
|---|---|
| Sodium lauryl ether sulphate | 7.0 |
| Sodium lauroyl glutamate | 4.0 |
| Decyl glucoside | 5.0 |
| Sodium cocoyl isethionate | 5.0 |
| Cationic guar | 0.5 |
| Sodium chloride | 1.5 |
| Citric acid/sodium hydroxide | q.s. to pH 5.5 |
| Preservative, fragrance | q.s |
| Water | to 100 |

The above composition has excellent creamy rich foam and conditions hair excellently in terms of combability and soft hair feeling.

EXAMPLE 4

| | % by weight |
|---|---|
| Laureth-6 carboxylic acid | 5.0 |
| Cocyl glucoside | 3.0 |
| Sodium lauroyl glutamate | 6.0 |
| Sodium cocoyl isethionate | 3.5 |
| Ethylhexyl glycerine | 1.5 |
| Lauryl alcohol | 0.7 |
| Polyquaternium-10 | 0.5 |
| Dimethicone | 0.5 |
| Ubiquinone | 0.1 |
| Isostearamide MIPA | 2.0 |
| PPG-9 | 2.0 |
| Citric acid/sodium hydroxide | q.s. to pH 5.0 |
| Preservative, fragrance | q.s |
| Water | to 100 |

The above composition improves hair volume, gives hair more elasticity in addition to the excellent creamy foam and conditioning effect in terms of combability, shine and soft hair feeling. Colour wash out effect was observed to be excellent.

EXAMPLE 5

| | % by weight |
|---|---|
| Cocoyl polyglucoside | 5.0 |
| Sodium cocoyl glutamate | 4.0 |
| Sodium cocoyl isethionate | 3.5 |
| Sodium laureth sulphate | 5.0 |
| Decyl glycerine | 1.0 |
| Decyl alcohol | 1.0 |
| Polyquaternium-67 | 0.8 |
| Dimethicone | 0.5 |
| PEG-160 sorbitan triisostearate | 1.0 |
| PPG-9 | 1.2 |
| Basic red 51 | 0.1 |
| Citric acid/sodium hydroxide | q.s. to pH 5.5 |
| Preservative, fragrance | q.s |
| Water | to 100 |

The above composition gives hair a red shine, and additionally delivers excellent conditioning effect in terms of more elasticity, combability, shine and soft hair feeling in addition to the excellent creamy rich foam. The composition foams very quickly.

The invention claimed is:

1. An aqueous cleansing composition for keratin fibres, the composition comprising
   (a) at least one first mono ester anionic surfactant selected from sodium cocoyl isethionate and ammonium cocoyl isethionate;
   (b) at least one second anionic amide surfactant;
   (c) at least one third anionic surfactant which is different from the first and second surfactants (a) and (b); and
   (d) at least one non-ionic surfactant selected from alkyl polyglucosides of the general formula $R_8-O-(R_9O)_n-Z_x$, wherein $R_8$ is an alkyl group with 8 to 18 carbon atoms, $R_9$ is an ethylene or propylene group, Z is a saccharide group with 5 to 6 carbon atoms, n is a number from 0 to 10 and x is a number between 1 and 5, wherein the at least one non-ionic surfactant is present at a concentration from 1 to 15% by weight, calculated to the total composition,
   wherein the composition is free of amphoteric surfactant and has a pH in the range from 2.5 to 6.5.

2. The composition according to claim 1, wherein the composition has a pH in the range from 3 to 5.5.

3. The composition according to claim 1, wherein the at least one second anionic amide surfactant is selected from the compounds according to the general structure

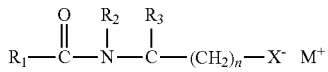

wherein $R_1$ is a saturated or unsaturated, straight or branched alkyl chain with 7 to 17 carbon atoms, $R_2$ is H or a methyl, $R_3$ is H, $COO^-M^+$, $CH_2COO^-M$ or COOH, n is 0 to 2, X is $COO^-$ or $SO_3^-$ and M is independently chosen from H, sodium and potassium.

4. The composition according to claim 3, wherein the at least one second anionic amide surfactant is selected from taurate, glutamate, alanin, alaninate, sarcosinate and aspartate.

5. The composition according to claim 4, wherein the third anionic surfactant is selected from the compounds according to the general structure $R_{40}(OCH_2CH_2)_nOSO_3M$ wherein $R_{40}$ is a straight or branched, saturated or unsaturated alkyl chain with 8 to 22 carbon atoms, with 10 to 18 carbon atom and 12 to 14 carbon atoms, n is a number between 1 to 4 and M is an alkali metal, chosen from sodium, potassium and ammonium.

6. The composition according to claim 1, wherein the composition comprises a total surfactant concentration from 5 to 50% by weight, calculated to the total of the composition.

7. The composition according to claim 5, wherein the composition comprises (a) the at least one first mono ester anionic surfactant at a concentration of 1 to 15% by weight, (b) the at least one second anionic amide surfactant at a concentration of 1 to 15% by weight and (c) the at least one third anionic surfactant at a concentration of 1 to 15% by weight, calculated to the total composition.

8. The composition according to claim 1, wherein the at least one non-ionic surfactant is selected from decyl polyglucoside, cocoyl polyglucoside and lauryl polyglucoside and
   is present at a concentration from 1 to 10% by weight, calculated to the total composition.

9. The composition according to claim 8, wherein the composition comprises at least one hair conditioning agent.

10. The composition according to claim 9, wherein the hair conditioning agent is selected from cationic polymers and is present at a concentration from 0.05 to 3% by weight, calculated to the total composition.

11. The composition according to claim 1, wherein the composition comprises at least one direct dye.

12. The composition according to claim 7, wherein the composition comprises (a) the at least one first mono ester anionic surfactant at a concentration from 3 to 10% by weight, (b) the at least one second anionic amide surfactant at a concentration from 3 to 10% by weight and (c) the at least one third anionic surfactant at a concentration from 3 to 10% by weight, calculated to the total composition.

13. An aqueous cleansing composition for keratin fibres, the composition comprising
   (a) at least one first mono ester anionic surfactant selected from sodium cocoyl isethionate and ammonium cocoyl isethionate;
   (b) at least one second anionic amide surfactant of the following structure

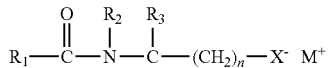

wherein $R_1$ is a saturated or unsaturated, straight or branched alkyl chain with 7 to 17 C atoms, $R_2$ is H or a methyl, $R_3$ is H, $COO^-M^+$, $CH_2COO^-M$ or COOH, n is 0 to 2, X is $COO^-$ or $SO_3^-$ and M is independent from each other and is selected from sodium and potassium; and
   (c) at least one third anionic surfactant which is different from the first and second surfactants (a) and (b),
   wherein the composition is free of amphoteric surfactant and has a pH in the range from 2.5 to 6.5.

* * * * *